United States Patent [19]

Brain

[11] Patent Number: 5,355,879
[45] Date of Patent: * Oct. 18, 1994

[54] LARYNGEAL-MASK CONSTRUCTION

[76] Inventor: Archibald I. J. Brain, St. Andrews, Abney Court Drive, Bourne End, Bucks SL 8 5DL, United Kingdom

[*] Notice: The portion of the term of this patent subsequent to Sep. 7, 2010 has been disclaimed.

[21] Appl. No.: 60,167

[22] Filed: May 7, 1993

Related U.S. Application Data

[63] Continuation-in-part of Ser. No. 952,586, Sep. 28, 1992, Pat. No. 5,241,956, and a continuation-in-part of Ser. No. 3,900, Feb. 1, 1993.

[51] Int. Cl.$^5$ ............................................. A61M 16/00
[52] U.S. Cl. ........................... 128/207.15; 128/207.14; 604/174; 604/96
[58] Field of Search ..................... 128/207.14, 207.15, 128/206.26, 207.16, 200.26; 604/96, 97, 98, 99, 100, 101, 102, 103, 174

[56] References Cited

U.S. PATENT DOCUMENTS

| | | | |
|---|---|---|---|
| 4,091,816 | 5/1978 | Elam | 128/207.15 |
| 4,454,887 | 6/1984 | Krüger | 128/772 |
| 4,497,318 | 2/1985 | Donmichael | 128/202.28 |
| 4,981,470 | 1/1991 | Bombeck, IV | 128/635 |
| 4,995,388 | 2/1991 | Brain | 128/207.15 |
| 5,033,466 | 7/1991 | Weymuller, Jr. | 128/207.15 |
| 5,038,766 | 8/1991 | Parker | 128/200.26 |
| 5,067,497 | 11/1991 | Greear et al. | 128/207.15 |
| 5,076,268 | 12/1991 | Weber | 128/207.15 |
| 5,116,305 | 5/1992 | Milder et al. | 600/18 |
| 5,241,956 | 9/1993 | Brain | 128/207.15 |

FOREIGN PATENT DOCUMENTS

| | | | |
|---|---|---|---|
| 2111394 | 7/1983 | United Kingdom | 128/207.15 |
| 2171017 | 8/1986 | United Kingdom | 128/207.15 |
| 2229367 | 9/1990 | United Kingdom | 128/207.15 |

Primary Examiner—J. Reed Fisher
Assistant Examiner—Eric P. Raciti
Attorney, Agent, or Firm—Hopgood, Calimafde, Kalil & Judlowe

[57] ABSTRACT

A shell of flexibly pliant material is in peripherally sealed engagement with the inflatable ring portion of a laryngeal mask such that when both the mask ring and the space within the shell are inflated, i.e., after patient installation of the mask in deflated condition, a back cushion is established with large-area self-adapting conformation to the back wall of the pharynx, so that inflation pressure in the back cushion not only positions back contours of the mask per se at offset from the back wall of the pharynx but in addition establishes a large area of uniformly distributed forward pressure on the mask per se, resulting in a pneumatically loaded application of the inflatable ring of the mask, into enhanced sealing conformance to and engagement with the laryngeal inlet.

15 Claims, 2 Drawing Sheets

LARYNGEAL-MASK CONSTRUCTION

This application is a continuation-in-part of copending U.S. patent applications Ser. No. 07/952,586, filed Sept. 28, 1992 now U.S. Pat. No. 5,241,956 and U.S. Ser. No. 08/003,900, filed Feb. 1, 1993, pertaining to laryngeal-mask constructions.

BACKGROUND OF THE INVENTION

Laryngeal masks, illustratively of the varieties disclosed in U.S. Pat. Nos. 4,509,514 and 4,995,388, are artificial airway devices designed to facilitate lung ventilation in an unconscious patent by forming a low-pressure seal around the laryngeal inlet. An inflatable-ring seal surrounds an appropriately shaped mask which fits into the lower pharynx and is attached to a tube which emerges from the mouth, as for connection to medical gas supply tubing.

In practice, these devices have been successful and are in daily use in hospitals throughout the United Kingdom. Such masks have been found to be effective in achieving a reliable airway, preventing obstruction in an unconscious patent. As presently used, such masks are especially effective in cases where difficulty with the airway is experienced. For example, the mask has been found to prevent contamination of the lungs by blood or debris following surgery of the nose and throat. But it has become apparent that an important contraindication to its use is the patient who is at risk from vomiting or regurgitation of stomach contents while unconscious. Said U.S. application Ser. No. 07/952,586 deals with this problem by providing an evacuation tube which is open through the center of the distal end of the inflatable seal of the laryngeal mask, thus utilizing the distal end of the inflatable ring as an inflatable cuff formation which establishes peripherally sealed engagement to the upper sphinctral region of the oesophagus and centrally supports the distal end of the evacuation tube. In addition, said U.S. patent application Ser. No. 07/952,586 discloses an additional inflatable cuff carried by the laryngeal mask and by the evacuation tube, for referencing inflation against the back wall of the pharynx, thus making it possible to establish the laryngeal-inlet seal with reduced inflation pressure, as compared with prior structures not having such an additional inflatable cuff.

Said U.S. patent application Ser. No. 08/003,900 is concerned with moulding techniques for manufacture of a variety of laryngeal masks; and, in conjunction with one of these, an inflatable back cushion is disclosed whereby the referencing inflation against the back wall of the pharynx is widely distributed, over substantially the full area of the laryngeal mask. Such a back-cushion construction has been found to be mechanically simple and highly effective, and it is desired to specifically disclose and claim the inflatable cushion in the context of each of several representative constructions, illustratively taken from the disclosures of said U.S. patent application Ser. No. 08/003,900.

BRIEF STATEMENT OF THE INVENTION

It is the primary object of this invention to provide inflatable back-cushion structure and action in conjunction with representative laryngeal mask configurations, whereby to achieve improved laryngeal-inlet sealing at reduced inflation pressure, and in general to avoid or materially reduce any chance of patient trauma by reason of installation or use of a laryngeal mask.

In its preferred embodiments, the invention achieves the foregoing object by applying a shell of flexible material in peripherally sealed engagement with the inflatable ring portion of a laryngeal mask such that when both the mask ring and the space within the shell are inflated, i.e., after patient installation of the mask in deflated condition, a back cushion is established with large-area self-adapting conformation to the back wall of the pharynx, so that inflation pressure in the back cushion not only positions back contours of the mask per se at offset from the back wall of the pharynx but in addition establishes a large area of uniformly distributed forward pressure on the mask per se, resulting in a pneumatically loaded application of the inflatable ring of the mask, into enhanced sealing conformance to and engagement with the laryngeal mask.

DETAILED DESCRIPTION

The invention will be described in detail for preferred embodiments, in conjunction with the accompanying drawings, in which.

Figure 1:
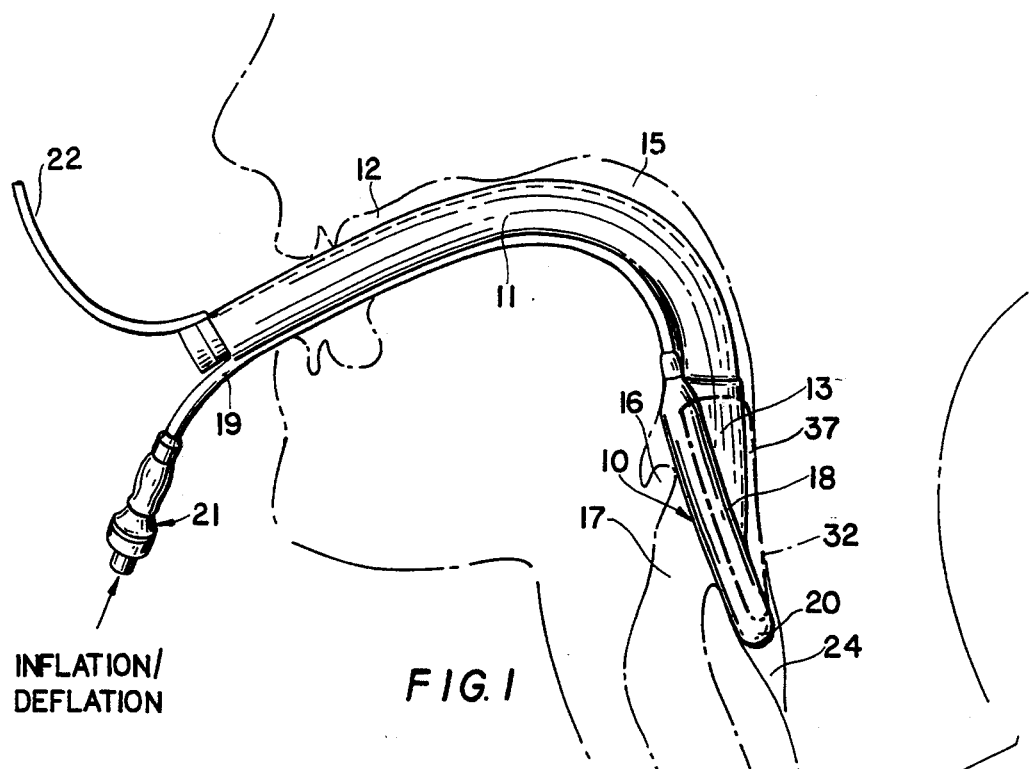
FIG. 1 is a diagrammatic view, generally in side elevation for a first embodiment of artificial airway device, having a laryngeal mask of simple construction, with the back-cushion feature of the invention but without provision for gastric drainage, the same being shown in inflated condition for use in a patient.
Figure 2:
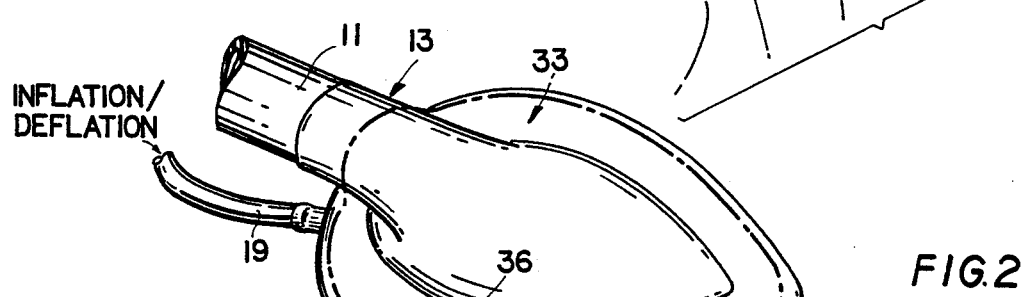
FIG. 2 is an enlarged and simplified view in perspective of the laryngeal mask of FIG. 1, shown for use of a single supply connection, for inflation/deflation control and actuation.
Figure 3:
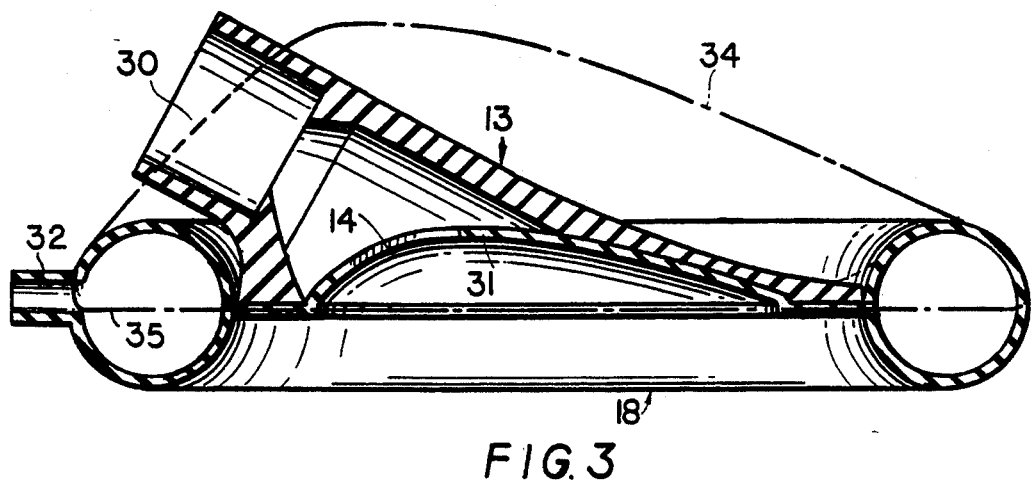
FIG. 3 is an enlarged view in longitudinal section of the laryngeal mask of FIGS. 1 and 2.

Referring first to the embodiment of FIGS. 1 to 3, the invention is shown in application to an airway system comprising a laryngeal-mask unit 10 and its airway tube 11, installed through the mouth 12 of a patient. The mask unit may be generally as described in said U.S. patents and therefore need not now be described in detail. It suffices to say that mask unit 10 comprises a body or back-plate 13 having a lumen 14 (FIG. 3) through which the airway tube 11 can establish a free externally accessible ventilating passage, via the patient's mouth 12 and throat 15, and past the epiglottis 16 to the larynx 17.

The body or backplate 13 of mask 10 may be of silicone rubber and relatively stiff; and body 13 is surrounded by an inflatable ring 18 which is generally elliptical and which is circumferentially united to body 13 in essentially a single plane. The inflatable ring 18 may also be of silicone rubber, although preferably relatively soft and flexible compared to body 13. An externally accessible flexible tube 19 is the means of supplying air to the inflatable ring 18 and of extracting air from (and therefore collapsing) ring 18 for purposes of mask insertion in or removal from the patient; check-valve means 21 in tube 19 will be understood to hold a given inflation or to hold a given deflation of ring 18. In the installed position of FIG. 1, the projecting but blunted distal end 20 of ring 18 is shaped to conform with the base of the hypopharynx where it has established a locating limited entry into the upper sphinctral region of the oesophagus 24. The inflated ring establishes a peripherally sealed closure around the laryngeal inlet, orienting the axis of the distal end of the airway tube 11 at an acute angle to the general plane of ring 18 and in substantial alignment with the axis of the laryngeal inlet, for direct airway communication with the larynx 17.

For the specific laryngeal mask construction of FIG. 3, the inflatable ring 18 is a first component part, and the body or backplate 13 is a separately moulded part adhesively assembled to ring 18. Various techniques may be employed to create ring 18, and the section shown is applicable for one of the embodiments of said U.S. patent application Ser. No. 08/003,900, to which reference is made for further descriptive detail. It suffices to identify the socket 30 of body 12, for assembly to the airway tube 11, the inlet port formation 32 for connection to inflation/deflation tube 19, and the thin pliant bowl formation 31 which defines the lumen 14 of the mask.

Figure 2A:
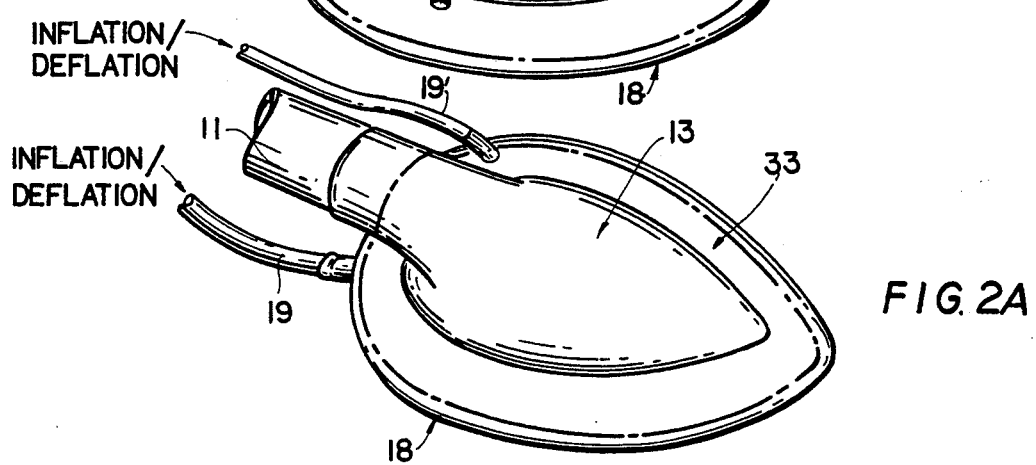
FIG. 2A is a view similar to FIG. 2, for the case of independent inflation/deflation control for the inflatable ring of the laryngeal mask and for the inflatable back cushion, respectively.

In accordance with the invention, and in the case of FIGS. 2A, a separately inflatable back cushion is established around and over the back side of body 13. To this end, a shell 33 of softly pliant material, inflatable to an envelope profile suggested by a phantom outline 34, is peripherally sealed and adhered to substantially the equator region 35 of ring 18, and this envelope is also open to the airway passage but at the same time peripherally sealed around the outer surface of the socket region 30 of body 13.

In the embodiment of FIG. 2, a local opening 36 in ring 18, and within the volume of the pliant envelope 34, enables inflation air via tube 19 to concurrently inflate (or to concurrently deflate) both ring 18 and the back cushion 33. And in the embodiment of FIG. 2A, there is no equivalent of the port 35, but a separate flexible-tube connection 19', which communicates only with the inner volume of the back cushion, enables independent control of inflation pressure to the respective inflatable volumes.

Regardless of whether the inflatable ring 18 and the inflatable back cushion are simultaneously or independently inflated, the net effect of inflation within both volumes, is to enable the back cushion 33 to establish referencing contact with the back wall of the pharynx, and the relatively stiff features of the back side of plate 12 are thereby substantially relieved from direct contact with the wall of the pharynx. In FIG. 1, this circumstance is shown by a heavy phantom profile of the back cushion, expanded for almost the full longitudinal extent of the mask ring 18 and in elongate continuous contact with the profile of the back wall of the pharynx, wherein adjacent profile features of the back side of body 12 are offset from the back wall of the pharynx, to the extent of a clearance 37. This offsetting clearance will be understood to extend over virtually the entire back area of the mask and its ring 18 because pressure within the back cushion will be operative on virtually the entire back area of the mask, driving the same, i.e., its ring 18, into forwardly loaded sealing coaction with the laryngeal inlet. Upon deflation, both inflatable volumes shrink, into conformance with features of body 12, with a floppy thin periphery of collapsed ring (18) material surrounding the base profile plate 12.

Figure 4:
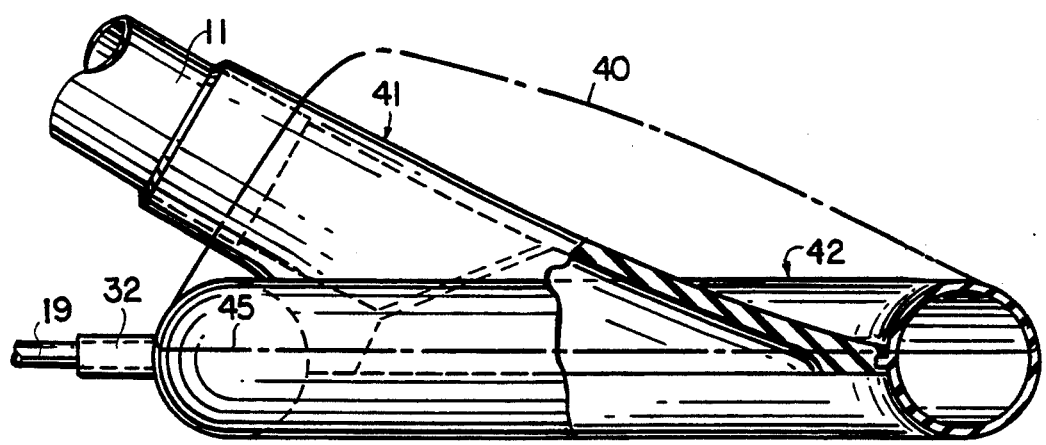
FIG. 4 is a view similar to FIG. 3 for a different laryngeal mask structure, wherein a side elevation has been partly broken-away to reveal detail of the longitudinal section.

In the embodiment of FIG. 4, the softly pliant shell 40 of the invention is applied to another one of the mask structures of said U.S. patent application Ser. No. 08/003,900, to which reference is made for descriptive detail. It suffices to indicate that the entire mask structure of FIG. 4 is the product of a single moulding operation, so that both the body part 41 and its peripherally connected inflatable ring 42 are integrally related. The back cushion material at 40 may be as previously described, namely, a shell sealed to substantially the full extent of equator 45 of ring 42. Inflation/deflation within or outside the body 41 is with the same cushion-loading action on the mask for enhanced sealing around the laryngeal inlet, and with the same backside clearance as previously indicated in connection with the offset 37 of FIG. 1.

Figure 5:
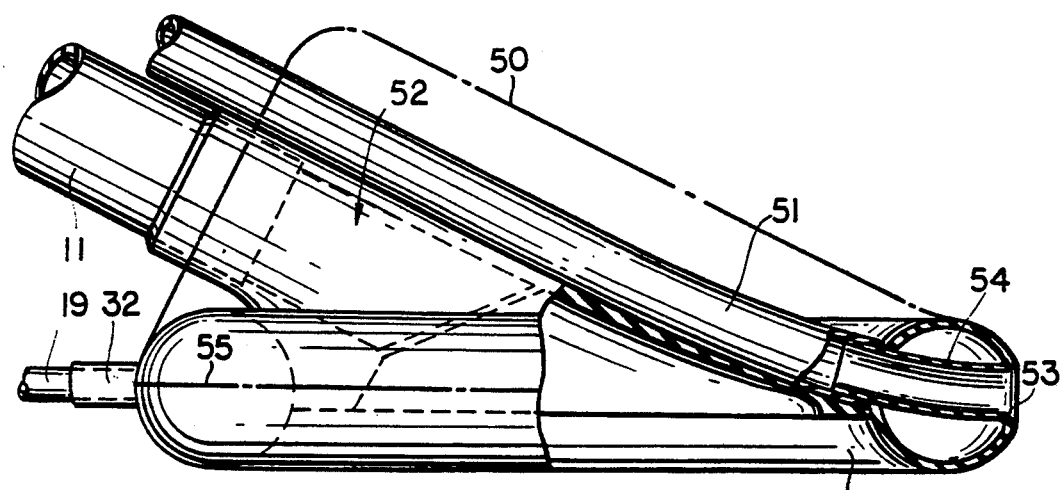
FIG. 5 is another side elevation, partly broken-away and in longitudinal section, for a further embodiment which incorporates a gastric drainage feature.

In the embodiment of FIG. 5, the softly pliant shell 50 of the invention is applied to still another one of the mask structures of said U.S. patent application Ser. No. 08/003,900, namely, a construction which features an evacuation tube 51 which extends alongside the airway tube 11 and the body 52 of a laryngeal mask. The evacuation tube 51 has sealed entry into and through the distal end of the inflatable ring 18 of the mask, via a re-entrant distal-end formation of ring 18; and tube 51 is thus centrally open at 53, where it is adapted to provide sealed and exclusive communication with the upper sphinctral region of the oesophagus. The evacuation tube 51 will be understood to be capable of being under applied reduced pressure, for prompt removal of a possible gastric discharge from the oesophagus, and this reduced pressure will be additionally understood to draw body tissue of the upper sphinctral region into enhanced sealing engagement with the distal end of the laryngeal mask. The pliant shell 50 will be understood to have sealed peripheral adherence to the equator region 55 of inflatable ring 18 and also to be sealed around the airway and evacuation structures, whereby to complete an inflatable back cushion which can establish a large-area of referencing support against the back wall of the pharynx. The ability of the inflated back cushion to enhance the sealing effectiveness of ring 18 around the laryngeal inlet is as described for other embodiments. And this enhanced effectiveness is achieved for a lesser level of inflation pressure than is possible without an inflatable back cushion.

While it is preferred that the pliant shell which is used to complete the inflatable back cushion of the various embodiments is shown and described as being peripherally adhered to the outer or equator region of the inflatable ring 18 of the mask, it will be understood that desired large-area back-cushion engagement with the back wall of the pharynx may also be obtained if the pliant shell is sealed to a lesser profile or contour of the back side of the mask, as to the peripheral region of body 13, along the line of peripheral juncture of body 13 to ring 18. In either event, the condition is satisfied that the effective area of the inflated back cushion is at least as great as the peripheral area of the mask body 13, along the line of peripheral juncture of body 13 to ring 18.

What is claimed is:

1. A laryngeal-mask construction, comprising a backplate member providing in essentially a single plane an apertured base-mounting rim of generally elliptical configuration, an inflatable toroidal ring of flexible material surrounding and continuously connected to said base-mounting rim, and an inflatable back cushion comprising a shell of flexible material adhered generally to the perimeter of said inflatable ring to define said back cushion in conjunction with said mask construction.

2. The construction of claim 1, in which an air passage communicates between said inflatable ring and said inflatable cushion, whereby a single means of inflation and/or deflation can simultaneously serve both said ring and said back cushion.

3. The construction of claim 1, in which said inflatable ring and said inflatable back cushion have independent connections for separate inflation and/or deflation.

4. The construction of claim 1, in which said back-plate member and said inflatable toroidal ring are separate components secured to each other.

5. The construction of claim 1, in which said back-plate member and said inflatable toroidal ring are integrally connected product components of a single molding operation.

6. The construction of claim 1, in which said back cushion has an effective area which is at least as great as the exposed surface area of said back-plate member at peripheral juncture to said inflatable ring.

7. A laryngeal-mask construction, comprising a back-plate member providing in essentially a single geometric plane an apertured base mounting rim of generally elliptical configuration, said back-plate member including an airway-tube connecting formation on an inclined axis that is at an acute angle to said geometric plane, the inclined axis being in a plane which includes the major axis of the elliptical configuration and which is normal to said geometric plane, an inflatable toroidal ring of flexible material surrounding and continuously connected to said base-mounting rim, and an inflatable back cushion comprising a shell of flexible material adhered generally to the perimeter of said inflatable ring and externally sealed around said airway tube connecting formation to define said back cushion in conjunction with said mask construction.

8. The construction of claim 7, in which an air passage communicates between said inflatable ring and said inflatable cushion, whereby a single means of inflation and/or deflation can simultaneously serve both said ring and said back cushion.

9. The construction of claim 7, in which said inflatable ring and said inflatable back cushion have independent connections for separate inflation and/or deflation.

10. The construction of claim 7, in which said back cushion has an effective inflatable area which is at least as great as the exposed surface area of said back-plate member at peripheral juncture to said inflatable ring.

11. The artificial airway device of claim 10, in which an air passage communicates between said inflatable ring and said inflatable cushion, whereby a single means of inflation and/or deflation can simultaneously serve both said ring and said back cushion.

12. The artificial airway device of claim 10, in which said inflatable ring and said inflatable back cushion have independent connections for separate inflation and/or deflation.

13. An artificial airway device to facilitate a patient's lung ventilation, comprising an airway tube, an evacuation tube and a laryngeal mask at one end of said tubes, said mask comprising a back-plate member providing in essentially a single geometric plane an apertured base mounting rim of generally elliptical configuration extending from a proximal end to a distal end, said back-plate member including an airway-tube connecting formation on an inclined axis that diverges proximally at an acute angle to said geometric plane, the inclined axis being in a plane which includes the major axis of the elliptical configuration and which is normal to said geometric plane, an inflatable toroidal ring of flexible material surrounding and continuously connected to said base-mounting rim, the distal end of said inflatable ring being configured for entry into and insertional location of the mask by engagement with the oesophagus at the upper sphinctral region of the oesophagus when the mask is positioned for sealing the airway tube to the laryngeal inlet, said evacuation tube including a portion having sealed passage through part of said toroidal ring and having an open distal end centrally within and axially short of the distal end of said ring, and an inflatable back cushion comprising a shell of flexible material adhered generally to the perimeter of said inflatable ring and externally sealed around said airway-tube connecting formation to define said back cushion in conjunction with said mask construction.

14. The artificial airway device of claim 13, in which said back cushion has an effective inflatable area which is at least as great as the exposed surface area of said back-plate member at peripheral juncture to said inflatable ring.

15. The artificial airway device of claim 13, wherein said evacuation tube includes a portion having sealed passage through part of said toroidal ring.

* * * * *